United States Patent [19]

DuBois et al.

[11] Patent Number: 5,229,110

[45] Date of Patent: Jul. 20, 1993

[54] PROCESS FOR PREPARING A VACCINE AGAINST MALARIA

[75] Inventors: Philippe DuBois, Antony; Jean P. Dedet, Cayenne Cedex; Thierry G. Fandeur, Cayenne Cedex; Serge Pauillac, Cayenne; Christian P. Roussilhon, Cayenne Cedex; Luiz P. Pereira de Silva, Paris; Jurg Gysin, Anglet, all of France

[73] Assignee: Institut Pasteur, France

[21] Appl. No.: 681,711

[22] Filed: Apr. 8, 1991

Related U.S. Application Data

[60] Division of Ser. No. 376,926, Jul. 10, 1989, Pat. No. 5,032,397, which is a continuation of Ser. No. 45,220, Apr. 29, 1987, abandoned, which is a continuation of Ser. No. 644,727, Aug. 23, 1984, abandoned.

[30] Foreign Application Priority Data

Dec. 27, 1982 [FR] France .................. 82 21817
Dec. 27, 1982 [FR] France .................. 82 21818
Jul. 28, 1983 [FR] France .................. 83 12496
Dec. 21, 1983 [FR] France .................. 83 20510

[51] Int. Cl.$^5$ .......................................... A61K 39/002
[52] U.S. Cl. ........................... 424/88; 530/403; 530/412; 530/820; 530/822
[58] Field of Search ............... 530/820, 822, 403, 412; 424/88

[56] References Cited

U.S. PATENT DOCUMENTS 4,466,917 8/1984 Nussenzweig .

FOREIGN PATENT DOCUMENTS 0062924 10/1982 European Pat. Off. .

OTHER PUBLICATIONS

Perrin et al.-Transactions of Royal Soc. Tropical Med. Hygiene vol. 75 No. 1 (1981) pp. 163–165.

*Primary Examiner*—Sam Rosen
*Attorney, Agent, or Firm*—Burns, Doane, Swecker & Mathis

[57] ABSTRACT

A process for preparing a vaccine against malaria comprising at least one polypeptide extracted from a schizont form of a strain of Plasmodium containing polypeptides antigenic to malaria. The polypeptides are recognized by immunoglobulin from a Saimiri Sciureus monkey resistant to the strain. The process includes the steps of:

(a) treating a preparation of a strain of Plasmodium with a solution of a detergent which is able to separate the cellular structures from the parasite proteinic constituents;

(b) recovering from the treated preparation, a polypeptide fraction having intact polypeptides of molecular weight ranging from about 70,000–85,000 or 90,000–120,000. The polypeptide fraction induces, in a first splenectomized Saimiri Sciureus monkey, a protective antibody against such strain, the polypeptides being recognized by immunoglobulin from a second Saimiri Sciureus monkey resistant to the strain. The immunoglobulin is capable, by an in vivo passive transfer to a third splenectomized Saimiri Sciureus monkey, sensitive to the strain, to protect the third monkey against the strain; and (c) adding a pharmaceutically acceptable vaccine.

17 Claims, No Drawings

PROCESS FOR PREPARING A VACCINE AGAINST MALARIA

CROSS REFERENCE TO RELATED APPLICATIONS

The present application is a divisional of application Ser. No. 376,926, filed Jul. 10, 1989, which is now U.S. Pat. No. 5,032,397, which is a continuation of application Ser. No. 045,220, filed Apr. 29, 1987, now abandoned, which, in turn, is a continuation of application Ser. No. 644,727, filed Aug. 23, 1984, now abandoned.

The invention relates to polypeptidic fractions inducing protective antibodies against malaria parasites, as well as immunogenic compositions containing them, expected to be suitable for the production of vaccines for man and animal. It is also pertaining to specific antibodies in vivo induced by these fractions.

The term "polypeptidic fractions" is used in the following disclosure for the convenience of language. It must not be interpreted in a restrictive way. This term can in fact encompass protein fractions or immunogenic fractions which have a chemical distinct structures for instance containing saccharadic or glycoproteinic or glycopeptidic antigens.

In other words, the term "polypeptide" means any peptidic or proteinic constituent, particularly of the protein or glycoprotein type, such as those which can be obtained from *Plasmodium falciparum* or parasites of malaria liable to infect man or primate.

It is known that in men or animals, which have been infected by malaria, and which have become resistant, there are antibodies directed against erythrocytic species of the parasites. The existence of these antibodies can be demonstrated by the protection which can be conferred at least temporarily to a non-immunized, sensitive or "naive" animal, by passive transfer to the latter from an immunoserum of an immunized animal or of purified immunoglobulins from this serum.

Several attempts to isolate a protective immunogenic principle from extracts of various species of parasites responsible for a corresponding form of malaria have been described in the technical literature. More recently, the hybridoma technology has enabled to isolate new antibodies liable to be used in the analysis of antigens of the malaria parasite constituents.

Thus YOSHIDA et. al. (1980) Science, 207, 71, have isolated an antigen liable to induce an immune response, protective with respect to rodents. Other laboratories have also resorted to the technology of hybridomas with the aim of isolating antibodies directed against certain species of *Plasmodium falciparum*, particularly liable to infect mice. Lines of hybridoma which secret antibodies, capable of inhibiting growth of the parasites in culture have been described by PERRIN et. al. (1981), Nature, 289-301. These authors have shown that the monoclonal antibodies which have been produced had inhibiting properties of a *P. falciparum* strain, capable of infecting mice, in a culture thereof.

An antigenic principle presented as being liable to be used for the constitution of vaccines against malaria has been described in the European patent application No. 71 705. This active principle obtained for instance from parasites of Plasmodium, presents the following characteristics:

1. its molecular weight is in the range of $1.8 \times 10^5$ to $2.5 \times 10^5$;

2. it is associated with the membranes of the erythrocytic schizont or merozoite forms of the parasite and 3. this antigenic principle is liable to be fragmented, within the infected erythrocytes, into discrete fragments presenting the same antigenic properties, said antigen or the fragments obtained therefrom being associated to the surface membrane of the merozoites.

Among the cited Plasmodium, some were *Plasmodium falciparum* of human origin.

The European patent application also discloses a process for isolating this antigenic principle, said process comprising solubilizing erythrocytes comprising schizont forms of the Plasmodium parasite, contacting the solubilized matter with specific monoclonal antibodies of the antigenic protein sought, and preferably fixed on a solid support to form an antibody-antigen complex, eliminating the proteins or polypeptides which are not engaged in the complex or not fixed and recovering the antigenic protein from the antibody-antigen complex. The monoclonal antibodies have been obtained from hybridomas chosen from among cellular hybrids, the latter having been obtained by fusion between cells of mice prealably immunized with the chosen parasite and myeloma cells.

Results showing the protective character of the antigenic principle thus obtained with respect to mice, have been actually-reported.

Although promising, these results must be considered with care. In fact, the infectious malarial parasites for man and primate are not generally infective to mice and conversely. It is not then possible to exclude that in the previously described system, the mouse immune system had recognized antigenic determinants contained in the extracts used for immunization, which however were not capable to induce really protective antibodies for primate or man. Of course, antigens have been obtained, which were recognized in vitro by human immune serum, for instance in immunoprecipitation experiments. Results as to their protective activity with respect to monkey or man, have not been reported.

The object of the invention is to provide for an improved immunogenic active principle liable to be obtained from various species of parasites known or liable to be found as being capable to infect man or primate, which are expected to be more suitable for human vaccination against malaria or paludism. It is also an object of the invention to provide a process for making such immunogenic principles.

The immunogenic composition according to the invention contains one or several polypeptides extracted from malaria parasites, infective to man, these polypeptides being more particularly characterized by their capacity to react with protective antibodies originating from monkeys resistant with respect to human malarial parasites and particularly to species of *Plasmodium falciparum*.

The invention brings into play the capability of parasites infectious in man, particularly of *Plasmodium falciparum*, of being adapted to Saimiri Sciureus (or Aotus trivirgatus, or Rhesus) monkeys and of causing an infection in monkeys which is identical in all respects to human infection.

The animals can be made resistant by an experimental infection, followed by an appropriate treatment, particularly by quinine. This resistance is directly linked to the fact that protective antibodies appear in these animals. It is recalled that the parasite which has been injected to a first monkey and then underwent successive passages in several monkeys, adapt thereto so as to become virulent for the monkey, and more particularly for the splenectomized monkey.

Particularly, the invention relates to polypeptidic fractions obtained from *P. falciparum* comprising polypeptides having average molecular weights ranging from about 72 000 to about 140 000.

which induce particularly in monkey, and more particularly Saimiri Sciureus monkey, active antibodies against malaria parasites, more particularly *Plasmodium falciparum* or parasites which present the same essential biological characteristics:

which are recognized by sera or other immunoglobulin compositions originating from animals, particularly Saimiri Sciureus monkeys, resistant to parasite, these sera or other compositions containing the corresponding immunoglobulins being capable, by in vivo passive transfer to animals sensitive to the parasite, to protect them against said parasite.

It is to be noted that the polypeptidic fractions are also recognized by antibodies originating from adults living in an endemic area and presenting a high degree of resistance to *P. falciparum*. The protective power of the serum from such persons has been demonstrated by experiments of passive transfer to children, infected with malaria (COHEN et al., 1961, Nature, 192, 733).

Advantageously, the immunogenic compositions of the invention are obtained from the strain of *Plasmodium falciparum* which has been deposited in the National Collection of Micro-organims Cultures of INSTITUT PASTEUR of Paris (C. N. C. M.) under no. FUPC I-212 on Dec. 23, 1982.

A first group of preferred polypeptidic fractions presenting the above mentioned properties are besides characterized by average molecular weights of 72 000, 76 000, 80 000 or 90 000 daltons. Particularly, preferred polypeptidic fractions of the invention present molecular weights of about 75 000±5 000.

Another group of preferred polypeptidic fractions of the invention pertains to polypeptidic compositions characterized by polypeptides presenting the following molecular weights: 90 000, 95 000, 100 000, 110 000, 115 000 and 130 000 daltons, within a complex group ranging from 83 000 to 140 000 daltons. The invention relates particularly to polypeptidic fractions having an average molecular weight from 100 000±10 000.

The invention also relates more particularly to fractions which are more purified and presenting molecular weights respectively contained in the ranges of 72 000±2 000 and 90 000±5 000 daltons.

The group of polypeptides of molecular weights previously mentioned can be recognized by metabolic incorporation of labelled amino acids for instance $^{35}S$ methionine.

A third category of polypeptidic fractions having immunogenic protective characteristics are characterized by average molecular weights of about 50 000±5 000. The invention relates more particularly, among these latter fractions, to the ones which cannot be recognized by metabolic incorporation of labelled aminoacids such as $^{35}S$ methionine.

The molecular weights above mentioned result from comparative measures in an electrophoretic system, on the one hand, of migration distances of the involved fractions and, on the other hand, of migration distances measured under similar conditions of peptides of known molecular weights, more particularly human IgG, bovin serum albumin (BSA), chicken albumin, 8-phosphorylase and myosin. Advantageously, the polypeptides and peptides used are radio-actively or non radioactively labelled, for instance with fluorescein isothiocyanate.

The invention also relates to preparations which are more purified, characterized by their capacity to react with monoclonal antibodies of $IgG_2a$ type, secreted by the hybridoma deposited at the CNCM on Dec. 20, 1983 under no. I-271 and obtained by cellular fusion of myelom (strain Sp2/O-Ag 14) and splenic cells of BALB/C mice immunized with fractions of average molecular weights of 100 000 daltons obtained from the above mentioned strain FUPC I-212. This monoclonal antibody reacts specifically with an antigen having a molecular weight of 90 000, specifically recognized by protective immunoglobulins obtained from an immunized Saimiri Sciureus monkey.

*Plasmodium falciparum* is well known of the specialists. The schizontes and merozoites of this parasite have already been used to achieve experimental vaccines against malaria, particularly for monkey (MITCHEL et al., 1977. Lancet, i, 1 335 and SIDDIQUI W. A., 1977, Science 197, 388). The biological results which have been observed for the monkey and reported in this latter article titled "An effective immunization of experimental monkeys against the human malaria parasite. *Plasmodium falciparum*" can be considered as being significant and can be extrapolated to the results which could be observed in man.

The capacity of this parasite of infecting Saimiri Sciureus monkeys is also well known (GYSIN et al., 1980, J. Parasitol. 66, 1 003). It has also been demonstrated that this animal shows a high humoral response (GYSIN et al., 1982, Ann. Immunol. (INSTITUT PASTEUR) 133D. 95) and that the protective antibodies are produced in the chronical phase of the infection (GYSIN et al., 1982, Parasite Immunol. 4, 421).

The invention thus relates to all the preparations obtained from infectious parasites for man or primate, liable to react with protective antibodies (serum, ascites caused in animal or more purified immunoglobulins obtained from said serum or ascites) obtained from immunized Saimiri Sciureus monkeys.

The presence of the protective antibodies in the serum of animal particularly monkey, can be appreciated by the protection induced by the serum of an immunized animal (or of the immunoglobulins which are extracted therefrom) to protect even but temporarily a non immunized animal, particularly a splenectomized animal, and sensitive with respect to parasite, particularly strain FUPC I-212, when this serum is passively transferred in vivo from the imunized animal to the non immunized animal.

Particularly, it is possible to use as a source of protective antibodies for the detection of polypeptidic fractions, according to the invention, sera, ascites or immunoglobulinic fractions obtained from monkeys and which are able, by in vivo passive transfer to sensitive splenectomized recipient monkeys, to protect the latter against parasitic infection when these have previously received, by route an injection of $50 \times 10^6$ of parasitized cells, obtained from splenectomized infected animals in the ascending phase of acute infection.

Preferably, recourse will be had to sera, ascites or immunoglobulinic fractions which enable this protection, when they are administered to the sensitive animal, at doses such that the blood content in immunoglobulins received by the recipient animal does not exceed 1 mg per ml. With Saimiri Sciureus, one may use as a source of protective antibodies the immunoglobulins which afford the above said protection in the recipient animal, when administered —from two to three days after infection— by intraperitoneal route, at the rate of daily doses of 3 to 10 mg of immunoglobulins, or by intravenous route, at the rate of daily doses of 0.5 to 2 mg of immunoglobulins, over a period of 3 to 6 days. The protective effect is itself assessed by the inhibition and the control which is then observed of parasitaemie during and after treatment, by counting (under microscope) the percentages of parasitized red blood cells in blood smears, colored by Giemsa.

The parasites which are used for the invention can be constituted by the above mentioned *P. falciparum* FUPC I-212 strain.

The immunized animals, particularly Saimiri Sciureus, are animals which may have been themselves exposed to infectious parasites and treated either by chemotherapy, for instance quinine, or by administration of protective immunoglobulins originating from another animal, which however was immunized.

Generally, these protective antibodies are present in animals in the infectious or chronical subinfectious stage. It is significant with respect to this fact, that the protective antibodies may not be present in significant amounts at the end of the acute infection period in the recipient animal, although at this time, high titres of anti-malarial antibodies can be detected in vitro by classical techniques of immunofluorescence. However, the protective antibodies appear within 30 to 90 days, from the end of the acute infection.

Besides, the presence of protecting antibodies cannot always be linked to the serum content in antibodies having an in vitro inhibiting activity. It is particularly to be noted that immunoglobulin preparations can, by in vivo passive transfer under the mentioned conditions, exhibit an important protective activity, while presenting no in vitro inhibiting effect against the parasite cultured in red blood cells of man or of Saimiri Sciureus monkey.

The source of immunoglobulins which can be used for detecting polypeptides according to the invention is either constituted by a whole serum containing said immunoprotective antibodies, or by the ascites which have previously been provoked in the protected animal, or by immunoglobulin fractions obtained from serum or from ascite.

The conditions under which the ascites can be formed are known.

It is hereafter recalled that these ascites can be, for instance, formed by intraperitoneal injection of emulsified Freund adjuvant in an appropriate saline solution.

More purified immunoglobulins can be obtained from serum or from ascite, in a way also known per se, for instance by passage of the fluid on a support, for instance that commercialized under the designation "Sepharose 48", to which protein A had been fixed previously. The fixation of immunoglobulins can be carried out in the presence of a phosphate buffer pH 7.4. The fixed immunoglobulins, after complete washing of the column with an appropriate buffer, for instance with PBS buffer, can then be eluted with 1M acetic acid, then neutralized, dialyzed against PBS and advantageously concentrated so as to reach a volume of the same order as the volume of serum or of ascite which had been resorted to.

An additional characteristic of the protective antibodies used in the detection of polypeptidic fractions according to the invention lies in their capacity to recognize not only high molecular weight polypeptides, for instance of about 200 000, among the dissolution products of the parasite, but also of the polypeptidic fractions of lower molecular weight according to the invention (having particularly molecular weights ranging from 75 000 and 100 000). In that respect, they distinguish over non-protective antibodies which recognize high molecular weights, but do not recognize the 75 000 and 100 000 molecular weights.

The invention also relates more particularly to "intact" polypeptides in that they are not constituted by fragments of membran proteins having higher molecular weights initially, synthesized at the stage of schizonts and then having undergone intracellular digestion. Particularly, polypeptides which are immunologically identical to preferred polypeptides of the invention (having a molecular weight of about 76 000) can be synthesized in a non cellular or "cell free" system, particularly in a rabbit reticulocyte lysate, by the in vitro translation of messenger RNA extracted from the parasite, in the schizont stage, under conditions where the synthesized proteins are made resistant to the trypsin digestion. The translation is advantageously carried out in the presence of microsomes of dog kidney, previously added to the lysate.

Similar observations can be made with polypeptides which are able to react with protective antibodies and presenting average molecular weights of 72 000, 76 000, 90 000, 100 000 and 110 000. These observations suggest thus that the messengers RNA resorted to, contain some which were specific of these polypeptides, so that these do not result, even during the intracellular translation of the corresponding messengers RNA, from the degradation of proteins presenting in fact higher molecular weights.

The invention also relates to a process for obtaining such immunogenic fractions. This process comprises treating a preparation which has been previously obtained from a malarial infectious parasite, particularly of the Plasmodium type, such as *Plasmodium falciparum*, with a solution of a detergent, such as sodium dodecylsulfate (SDS) or the one known under the designation of Triton X100, or alike, liable to induce the dissolution of the main part of the cell structures and of the proteinic constituents of the parasite, separating and recovering from the solution which has been formed, those of the polypeptides which present the above mentioned average molecular weights or contained in the average molecular weights which have been above mentioned and which contain immunogenic polypeptides capable of inducing the production of protective antibodies against infectious parasites against man and/or monkey as well as of being recognized by protective antibodies obtained from immunized monkeys.

An additional purification can be obtained by reaction with protective antibodies or equivalent antibodies which have been previously fixed to a soluble support. The term "Equivalent antibodies" as meant herein designates antibodies which have been previously formed and are able to react with the same immunogenic peptides. They consist for instance of monoclonal antibodies obtained from hybridoma resulting from cellular fusions between competent spleen cells obtained from mice immunized against one of the above said polypeptides and of appropriate myeloma cells. The immunogenic polypeptides which are retained in a complax with the antibody used are then recovered for instance by a technique similar to that referred to above in the disclosure of an example of enrichment of the immunoglobulins contained in a serum or an ascite of an animal immunized against a parasite.

Advantageous antibodies are obtained from hybridoma which were formed from cells of mice which had been immunized against one of the polypeptides which both induce the production of antibodies protective against infectious parasites and recognized by protective antibodies obtained from immunized monkeys. A preferred monoclonal antibody to achieve the purification of one of said polypeptides according to the invention is obtained from the hybridoma deposited in the CNCM under no. I-271.

Alternatively, immunogenic fractions according to the invention can also be obtained from the above said solution of the cellular structures and of the proteinic constituents of the parasite, by contacting said solution directly with a fixed antibody, such as above defined, dissociating the obtained complex so as to recover the fixed antigens and, if deemed desirable, separating and recovering the different immunogenic polypeptides present, according to their respective molecular weights.

The invention is not limited to the above said fractions. It also encompasses the polypeptidic fractions which can be obtained from the parasites which can be considered as derived from or even mutants of *Plasmodium falciparum*.

The invention also extends to immunogenic polypeptides, which are recognized by protective antibodies, obtained from animals which are resistant to the strain of *Plasmodium falciparum* deposited in the CNCM under no. FUPC I-212 on Dec. 23, 1982 and to the polypeptides which are recognized by the more specific antibodies obtained from animals which have been immunized with the protective polypeptides according to this invention and originating from the same FUPC I-212 strain.

The polypeptides obtained from infectious malarial parasites, whatever their origin, are also included within the frame of the present application to the extent they are both protective and recognized by monoclonal antibodies secreted by the hybridoma formed under conditions which have already been mentioned, obtained from donor animals immunized against polypeptides according to the invention and obtained from the FUPC I-212 strain.

This is particularly the case for polypeptides originating from strains other than *P. falciparum* and which are recognized by monkey protective antibodies and possibly by the monoclonal antibody which is secreted by the above identified hybridoma I-271. By way of examples of "sources" of polypeptides according to the invention, one may mention *P. vivax, P. ovale, P. chabaudi, P. voelli, P. knwolesi*, etc.

Generally, it will be possible from a given preparation of parasites, to determine those of the proteinic constituents which are liable to induce in vivo the production of protective antibodies according to the following procedure.

The starting material is a culture of the parasite under study previously obtained within a culture medium containing a radio-active label which is specific of proteinic constituents of the involved parasites, such as $^{35}S$ methionine. The parasitic constituents are then collected and treated as it has been above described with respect to *Plasmodium falciparum* or in a more detailed way in the examples thereafter. But in order to dissolve the major part of the cellular and proteinic constituents of the chosen parasite, the detergent Triton ×100 is used instead of SDS. Triton ×100 causes the solubilization of antigenic proteins without deeply modifying their structure, so that they can always be recognized by antibodies. Then the following operations are carried out.

First series of operations a) An electrophoresis of a sample of all the proteinic constituents of the parasites is carried out.

A series of strips which can be visualized by autoradiography is obtained. By comparison with the proteins, the molecular weights of which are known, the sequence of molecular weights is determined according to the migrations also measured for peptides of known molecular weights.

b) Starting from a distinct sample of the above said proteinic constituents (the preparation involved is the labelled one) it is reacted with a serum containing protective antibodies originating from a monkey, resistant to the parasite; the resulting mixture is then reacted with protein A of *S. aureus* (commercial preparation).

The precipitate which is formed is separated by centrifugation; this precipitate contains a radioactive protein A-antibody-antigen-complex.

After washing of the precipitate, it is dissolved again in the presence of SDS. The latter dissociates the antigen from the antibody and from the protein A. The whole mixture is then subjected to an electrophoresis and the labelled strips, in a smaller number than in the preceding case, as well as their respective molecular weights are determined.

Second series of operations

The steps a) and b) above described are repeated, but using antibodies originating from a monkey sensitive to parasite.

By comparison of the strips which have been obtained on the gels after the reactions with sera originating from resistant animals, on the one hand, and of those obtained after reaction with sera originating from sensitive animals, on the other hand, the strips are determined which have been obtained only at the end of step b) of the first series of operations. Their ranges of molecular weights are determined too.

These strips contain proteinic constituents which are preferably recognized by sera of resistant animals and, accordingly, the antigens which are specifically recognized by protective antibodies.

Third series of operations

A new culture of the same parasite is carried out but in the absence of the radio-active tracer and a new electrophoretic separation of its proteinic constituents is carried out under the same conditions as in the first and second series of operations. The capacity of the constituents to induce in vivo the production of protective antibodies which have migrated at the same distances as the ones which have been recognized by the antibodies at the end of the second series of operations is then tested, and the constituents providing a positive immunological response are recovered, for instance as disclosed in relation to the above mentioned active proteinic constituents of *Plasmodium falciparum.*

The active constituents which have thus been isolated constitute the equivalents of protective polypeptides which have been described more particularly hereabove and as such are encompassed by the claims.

Additional characteristics of the invention will appear again in the description which follows of examples of production of polypeptidic fractions according to the invention and of the biological properties thereof.

EXAMPLE I

Culture of parasites and preparation

The parasites are cultivated on human red blood cells of group A+ in a RPMI 1 640 medium (FLOBIO) to which 10% of human serum of the same group had been added, under an atmosphere containing 1% of $O_2$, 3% of $CO_2$, 96% of $N_2$ (% in volume).

The cultures are sychronized at the stage of "rings" such as defined in the article of Science, 1976, 193, 673 by treatment with sorbitol (LAMBROS 1979, vol. 65, p. 418, J. of Parasitology). They were collected 40 hours later when the parasites reached the stage of mature schizonts with an average of 8 nuclei.

The red blood cells were washed by centrifugation with RPMI 1 640 and lysed by action of 0.025% Saponine with RPMI (% in weight) in the presence of protease inhibitors "PMSF", "TLCK" (SIGMA) $10^{-3}$M, for 10 minutes at 37° C.

The free parasites are purified by centrifugation in a discontinuous gradient in PBS comprising 40 to 70% of PERCOLL (PHARMACIA), for 30 minutes at 4° C. The 40-70% interface is recovered with a pipete and washed 2 to 3 times with PBS.

Preparation of semi-purified proteins

The parasites are treated by 5 to 10 volumes of an electrophoresis buffer containing 6% by weight of SOS and 10% of beta-mercapto-ethanol (or of an analogous agent liable to break the disulfide bridges of proteins and to linearize the polypeptidic chains) twice for 5 minutes at 100° C.

The extracts were centrifuged 5 minutes at 15 000 g, the supernatants (containing more than 90% of total proteins initially contained in the parasites) were submitted to an electrophoresis (for 4 hours under 200 V) on a gel containing 10% in weight/volume of acrylamide within an aqueous Tris buffer (at pH 8-9) containing 0.2% of SDS (in weight/volume).

After electrophoresis, strips of gel were cut at the levels corresponding to the molecular weights 75 000±7 500 daltons as detected on the gel by simultaneous electrophoresis of labelled peptides with fluoresceine isothiocyanate (human IgG, BSA, ovalbumine, B phosphorylase and myosine). In the same way, the gel strips which contain the polypeptides presenting average molecular weights of 100 000±10 000, were cut and collected in a dialysis bag. The protein concentration is determined by colorimetric titration of proteins ("Biorad Assay", kit commercialized by BIORAD and described by SPECTOR. Analytical Biochemistry, 1978, 86, 142).

The preparations which were finally obtained were analyzed by electrophoresis on polyacrylamide SDS gel and revealed by coloration with $AgNO_3$. It was thus still possible to prepare, from the preparation of polypeptides having molecular weights of 75 000±5 000:

3 major bands in the range of molecular weights:

72 000, 76 000, 80 000 daltons;

1 minor band in the range of molecular weights:

90 000 daltons.

Minor degradation products of this strip of 75 000 were found in the ranges of 33 000 and 45 000 daltons.

It was also possible to prepare under the same conditions, from the fraction of molecular weights of 100 000±10 000, isolated major bands in the following ranges of molecular weights: 40 000, 45 000, 100 000, 110 000, 115 000 and 130 000, among a wide complex group, ranging from 83 000 and 140 000. Minor degradation products of this band were found in the areas of 33 000 and 45 000 daltons.

The biological properties of these fractions, be it those of average molecular weights of 75 000 or 110 000, or of the more purified proteinic fractions, which can be isolated from the preceding ones, can be evidenced as hereafter described. The results which follow have been obtained with the 75 000 and 100 000 fractions, before additional purification.

Test of Saimiri Sciureus monkey immunization

The immunization results liable to be obtained with these primates are particularly significant of what could be similarly obtained with man. These animals can be made even more sensitive to the parasite infection by splenectomy: the infection develops quicker in splenectomized monkeys: It is manifested by important parasitaemie (about 50% of their red blood cells can be infected with the parasite). The splenectomized animals which have been infected with malaria die within about 10 days.

The following tests have been carried out with splenectomized animals respectively separated in two groups of 5 and 10 monkeys.

The animals of the first group were inoculated three times with each time a dose of 100 μg of preparations to be tested, diluted in 0.5 ml of PBS, emulsified with an equal volume of Freund adjuvant, complete for the first inoculation, incomplete for the two following ones.

These inoculations were carried out at a time interval of 3 weeks, in the form of subcutaneous injections.

The monkeys of the second groups (control) received only adjuvants.

Three weeks after the third immunization, the animals were infected with $50 \times 10^6$ parasitized red blood cells, by intravenous route. The parasitaemie was then monitored each day for three weeks. An important delay of the parasite multiplication was observed in the animals which had been imunized. 15 days later, the proportion of parasitized red blood cells in immunized animals was lower than 10%, whereas in the control group the parasitaemie was over 25%, five days after the last injection. Similar results were obtained with the two preparations.

These results were are highly significant taking into account the splenectomized character of animals. Similar results were obtained with more purified fractions.

EXAMPLE II

Culture of parasites and preparation

The parasites (coming from the strain P. falciparum, CNCM no. FUPC I-212) were cultivated on human red blood cells A+, according to the technique described by GYSIN et al. (Les Ann. Immunol. -INSTITUT PASTEUR-1330, 95-102, 1982) and synchronized by the sorbitol technique as described by LAMBROS et al. (J. Parasitol. 65, 418-420, 1979).

The infected cultures were collected when the parasitaemie reached 5 to 10% of cells and when the cells reached the stage of schizonts. After two washings with RPMI 1 640 (GIBCO) medium, the red blood cells were lysed with Saponine (0.025% by weight) for 10 minutes at 37° C. The suspension was then cooled and centrifuged at 3,500 g for 10 minutes. The sediment was then resuspended in RPMI 1,640, introduced into a PERCOLL gradient (product manufactured by PHARMACIA) (20–40%), then centrifuged at 3,500 g at 4° C. for 30 minutes. The free parasites were collected at the interface 20/40, washed twice in PBS buffer and frozen at −20° C., in the presence of protease inhibitors, such as those commercialized under the designation TLCK and PMSF (SIGMA).

Preparation of immunogenic semi-purified proteins

The preparations of parasites (20/40) were introduced into 5 volumes of a buffer solution (Tris 0.0625M, pH 6.8, 6% dodecylsulfate, 5% mercaptoethanol, 5% glycerol) boiled for 5 minutes and centrifuged at 150,000 g for 10 minutes.

The supernatant was applied to a SDS-polyacrylamide gel, parallely with reference peptide of determined molecular weights labelled with fluoresceine isothiocyanate (bovine albumin serum, rabbit IgG and ovalbumine), B-phosphorylase and myosin. After migration through the gel, the bands of molecular weights corresponding to the ranges of 70 000–85 000 and 90 000–120 000 respectively (with respect to the migration of reference peptides) were cut. The proteins were then eluted from these gel strips by electrophoresis in a Tris-glycine-buffer, pH 8.6 and containing 0.1% in weight of SDS, and collected in a dialysis bag. The protein concentration was determined by colorimetric titration of proteins, Coomasie blue method, "Biorad Assay", kit commercialized by BIORAD and described by SPECTOR "Analytical Biochemistry", 1978, 86, 142.

Fractions I and II were thus obtained, which have been further used in the immunization tests hereafter described. These fractions contain about 100 μg of proteins/20 mg of protein contained in the original raw extract.

These fractions turned out to contain distinct molecular weight bands, when they were submitted to a new fractionation in a 7% polyacrylamide SDS gel. Fraction I has revealed to contain 4 major polypeptidic bands of molecular weights of 72 000, 75 000, 85 000 and 90 000 and fraction II has revealed to contain essentially 5 average molecular weight bands of 90 000, 96 000, 100 000, 105 000 and 120 000 respectively.

The presence of minor bands averaging 50 000daltons was detected in both preparations.

Test of squirrel monkey immunization

Groups of 5 splenectomized animals received three subsequent subcutaneous injections at day 0.21 and 41. Each injection consisted of 100 μg either of fraction I or of fraction II contained in an emulsion formed from a saline phosphate buffer solution and containing 0.1% of SDS and a same volume of complete Freund adjuvant (for the first injections) or of incomplete Freund adjuvant (for the following injections). Ten control animals received only the saline phosphate-buffer-solution (PBS) containing 0.1% of SDS with complete or incomplete Freund adjuvant, as required by the same protocol of administration. Blood samples were periodically collected, after and during vaccination, and examined as to their hematological, parasitological, microbiological and serological characteristics. The animals have supported the vaccination quite well. No injury has been observed at the injection sites. The monkeys have always looked healthy and showed a normal activity. No anemy has been detected either in the vaccinated animals or in the control animals.

Antimalarial antibodies, measured by indirect immunofluorescence, have been detected just after the second injection.

The animals received, by intravenous injection, $50 \times 10^6$ parasites (FUP strain) at day 55. After this trial, the parasitaemie were measured daily on colored samples with Giemsa reagent. The acute parasitaemie which developped in 9 animals out of the 10 control animals required a quinine chemotherapy within the following eight days, to avoid death. Among five animals which received fraction I, one presented a response similar to the controls. The other four animals showed a high resistance to challenge. A marginal parasitaemie was observed in two of them. In the other two animals, the parasitaemie reached 5% but disappeared completely in the following three weeks. The five animals which have been immunized with fraction II have all presented a good resistance to challenge. An increase of 10% of parasitaemie has been observed at the tenth day after challenge for only one of the animals. Yet, this parasitaemie decreased within the following three weeks.

Control smears have then been carried out twice a week within the two months following the challenge. The measures yielded negative results in all the vaccinated animals, whereas an increase of parasitaemie has been observed with 5 of the control animals which had been treated with quinine, after interruption of the treatment, so that they must have been submitted to a second cycle of chemotherapy. All the animals which have been infected by the parasite (vaccinated animals and control animals) have presented in the first weeks an anemy with an average 30% drop of the red blood cell rates. The anemy has yet been delayed in the vaccinated animals. Besides, the hematocrites resumed a normal value 4 weeks after the challenge. The weight variations of animals before and after the vaccination have not exceeded 2%.

The humoral answer of the monkeys to the different immunizations has been appreciated by immunoprecipitation carried out between extracts of parasites labelled with $^{35}S$ methionine, and samples of serum taken from all the animals before immunization and from the control animals, before the challenge by the live parasite. In animals immunized by fraction I as well as by fraction II, essentially homogenous responses against principally two polypeptides of molecular weights of 72 000 and 90 000 and weaker responses against peptides of molecular weights of 96 000 and 100 000 have been observed.

A protein band was observed in the area of molecular weight 110 000, for the animals which had been vaccinated with fraction II. No answer has been observed, at least under the experimental conditions, with respect to the 76 000 band contained in the original fraction I. This last observation finds perhaps its explanation in the modification of the antigenic determinants presented by the protein corresponding to that molecular weight in the live parasite, in the course of the purification stages described above. The responses, which can be compared and which have been observed in the two groups of immunized animals, lead to think that there is an important antigenic relationship between the proteins of the two fractions, relationship which possibly explains the comparable resistance degree against the parasite, which has been observed in the two groups.

The preceding results show the important vaccinating capacity of the fractions of the invention. This result is all the more remarquable as this vaccination has been obtained with proteins of parasites which have been denatured by SDS. The chemical denaturation of said proteins by detergent does not cause the loss of vaccinating properties thereof.

The peptidic fractions according to the invention constitute, first of all, biological reagents of particular interest in that they are active in vivo. They can be used as standards for in vivo activity of other immunogenic preparations obtained from parasites responsible for the various forms of malaria.

A more thorough purification of the vaccinating antigen contained in the above said fractions can be undertaken as described in the examples above. The invention relates more particularly to molecular weight fractions of 72 000 and 90 000.

The fractions of the invention, more purified or not, including the fractions of molecular weight of 50 000, can be also used as reagents for diagnosis and/or titration of antimalarial antibodies. In their use as reagents for diagnosis, it is possible to resort to classical techniques, for instance ELISA technique. The principle of that assay is hereafter recalled. It comprises for instance the following steps:

depositing determined amounts of peptide according to the invention in the wells of a microplate such as used in the ELISA method:

introducing increasing dilutions of serum possibly containing antibodies to be detected or to be titrated in the wells of this microplate;

incubating the microplate and contents:

thorough washing of the microplate with an appropriate buffer;

adding to the wells labelled antibodies directed against the first one, the labelling being achieved by means of an enzyme or of a fluorescent molecule, said enzyme being selected among those which hydrolyse a substrate, the hydrolysis of which entails an absorbance variation for a given wave length radiation;

measuring the absorbance variation or level of fluorescence, as appropriate; and determining, preferably comparative to similar measures carried out with a control, the antibody content of the studied serum.

The invention relates more particularly to a kit of diagnosis of malaria containing more particularly:

one of the fractions which has been defined herein said fraction being labelled either by an enzyme or by a fluorescent molecule;

specific antibodies with respect to the polypeptide used;

buffers and substrates, where appropriate, for revealing the label. The kit can also allow watching the evolution of the sickness in the patient by titration of the antibodies and of the parasites which are present in its blood.

Needless say that any other label may be used in the abovesaid assay on kit, including radioactive label.

It is appropriate to underline that the antigen of molecular weight of 72 000 is immunoprecipitated with anti $P.$ vivax, anti $P.$ ovale, anti $P.$ chabaudi immune sera. This antigen appears as a component common to different species of Plasmodium.

By way of example, there were incubated a polypeptidic extract of $P.$ chabaudi which has been labelled by $^{35}S$ methionine (300 000 cpm) with 10 $\mu$l of anti $P.$ falciparum immune serum obtained after immunization of Saimiri Sciureus or of a patient resistant to $P.$ falciparum and living in an endemic area or immunized mice with the fraction according to the invention. The analysis of the immunoprecipitated strips on gel revealed a 72 000 dalton antigen produced by $P.$ chabaudi.

A similar observation was carried out with the fraction of molecular weight of 90 000 prepared from $P.$ chabaudi.

These results are particularly interesting in so far as they show that the antigenicity at least of some of the polypeptides of this invention and obtained from these various Plasmodiums are not species-specific. It is particularly to be noted that $P.$ chabaudi is a Plasmodium which develops in mouse. Consequently, the use of antigenic polypeptides originating from $P.$ chabaudi or from any other Plasmodium which develops in small animals will be particularly advantageous, in as much as the culture of this Plasmodiae is cheaper than that the one of $P.$ falciparum, one of the natural hosts of which is the big monkey.

The invention relates more particularly to vaccinating compositions containing said polypeptidic fractions in association, as it has been mentioned, with various pharmaceutical vehicles and/or additive agents conventionally used in vaccine compositions. They may contain, by way of example, from 0.5 to 10 mg, particularly 1 to 5 mg of immunoglobulins.

The invention relates preferably to injectable solutions of said polypeptidic fractions, particularly for intravenous or intramuscular administration.

The polypeptidic fractions according to the invention can be used also for the preparation of antibodies which are more specific with respect to $P.$ falciparum than the sera or purified fractions of immunoglobulins which can be obtained from animals which have become resistant. It will be advantageous to resort, for the preparation of these more specific antibodies, to the technique of preparation of cellular hydrids or hybridomas comprising the following essential steps (liable to be carried out according to techniques which are now known):

fusion of myeloma cells and of splenic cells of mouse or of rat, even of monkey, which have been previously immunized with the above defined peptidic fractions:

selection among the formed hybridoma of those which secrete active monoclonal antibodies against the above said peptidic fractions.

These more specific antibodies, particularly these monoclonal antibodies, can then be used in turn, for instance to constitute columns of affinity chromatography. Such a column is for instance obtained by fixation of these monoclonal antibodies on the resin commercialized by PHARMACIA under the trademark Sepharose by the well known method with cyanogen bromide. These affinity chromatography columns can then in turn be used to achieve the separation of immunogenic peptidic fractions either from solutions obtained from preparations of parasites which have been treated with dissolving agents, of the type of those which have been above mentioned or from already concentrated fractions for which a higher purity is sought.

As is obvious and as it results from the foregoing, the invention also extends to all the alternatives and to all the compositions presenting similar immunological properties. In particular, the invention relates to all the immunogenic peptidic fractions liable to be obtained from other Plasmodiums, particularly *P. vivax, P. ovale* and *P. chabaudi, P. vaelli* and *P. knowlesi*, already mentioned, by using processes similar to those already described. It is important to emphasize that any Plasmodium may be used, no matter whether infectious for man or not.

Generally, the invention relates to immunogenic polypeptides liable to be obtained from any Plasmodium, from any variants and mutants of these Plasmodiae, as soon as these polypeptides are recognized by antibodies formed more particularly against above defined fractions. The invention also relates to immunogenic peptides of lower molecular weights, for instance immunogenic peptides resulting from a partial hydrolysis of the preceding peptides, in so far as this hydrolysis does not alter the immunogenicity sought. Any conjuguate between one of the immunogenic peptides which have been encompassed hereabove and a carrier molecule are also within the frame of the invention, each time that such a coupling can be required to strengthen the immunogenicity of the involved peptides.

Generally, the invention also relates to polypeptides meeting the conditions above defined and which could be recognized by monoclonal antibodies which have been formed previously against each of these polypeptides corresponding to average molecular weights which have been mentioned, particularly 75 000 and 100 000, or corresponding also to purified fractions, the constituents of which would be in major part formed of polypeptides having molecular weights of about 72 000, 75 000 (or 76 000), 85 000, 90 000, 96 000, 100 000, 105 000, 120 000. It results, of course, of the preceding that these hybridomas can be formed by the method of Köhler and Milstein which has become classical. The final selection of the hybridoma which secret the monoclonal sought antibodies is then particularly based on the detection of antibodies which recognize the polypeptides having molecular weights corresponding to those having initially been used for the production of the corresponding hybridomas and which are also recognized by the protective antibodies obtained from monkeys which have become resistant to parasites of malaria or by human serum originating from immunized persons living in endemic areas and presenting a high resistance power to plasmodiae.

We claim:

1. A process for preparing a vaccine against malaria comprising at least one polypeptide extracted from a schizont form of a strain of Plasmodium containing polypeptides antigenic to malaria, said polypeptides being recognized by immunoglobulin from a Saimiri Sciureus monkey resistant to said strain, comprising the steps of:
   a) treating a preparation of a strain of Plasmodium with a solution of a detergent which is able to separate the cellular structures from the parasite proteinic constituents; and
   b) recovering from the treated preparation, a polypeptide fraction having intact polypeptides of molecular weight ranging from about 70,000–85,000 or 90,000–120,000; said polypeptide fraction inducing, in a first splenectomized Saimiri Sciureus monkey, a protective antibody against said strain; said polypeptides being recognized by immunoglobulin from a second Saimiri Sciureus monkey resistant to said strain; said immunoglobulin being capable, by an in vivo passive transfer to a third splenectomized Saimiri Sciureus monkey, sensitive to said strain, of protecting said third monkey against said strain; and
   c) adding a pharmaceutically acceptable vaccine vehicle.

2. The process of claim 1, further comprising separating protective polypeptides having an average molecular weight of 75,000±5,000.

3. The process of claim 1, further comprising separating protective polypeptides having an average molecular weight of 100,000±10,000.

4. The process of claim 1, further comprising separating protective polypeptides having a molecular weight of 50,000.

5. The process of claim 1, wherein the detergent comprises a sodium dodecyl sulfate solution.

6. The process of claim 1, further comprising a gel filtration or electrophoresis step to recover polypeptides having the corresponding molecular weights.

7. The process of claim 6, wherein the polypeptides recovered have molecular weights ranging from 72,000 to 85,000.

8. The process of claim 6, wherein the polypeptides recovered have molecular weights ranging from 90,000 to 120,000.

9. The process of claim 1, further comprising contacting the solution resulting from the treatment of the parasite with the detergent, with protective antibodies fixed on a non-soluble support and eluting the antigen from the complex formed between the fixed antibodies and the corresponding antigen.

10. The process of claim 1, further comprising both a gel filtration or electrophoresis step, and a step comprising contacting the detergent-treated solution with antibodies.

11. The process of claim 9, wherein the fixed protective antibodies are replaced by monoclonal antibodies.

12. The process of claim 11, wherein the monoclonal antibody is directed against one of the protective polypeptides of molecular weight 50,000, 72,000, 85,000, 90,000, 96,000, 100,000, 105,000 or 120,000.

13. The process of claim 12, wherein the monoclonal antibody is directed against the polypeptide with an average molecular weight of 90,000, said monoclonal antibody corresponding to the one which is secreted by the hybridoma which has been deposited at CNCM under no. I-271.

14. A process for preparing a vaccine against malaria comprising at least one polypeptide extracted from a schizont form of a strain of Plasmodium containing polypeptides antigenic to malaria, said polypeptide protecting non-immunized Saimiri Sciureus monkeys, against virulent Plasmodium parasites, infectious for man, such as *Plasmodium falciparum*, comprising
   a) treating an aqueous solution of water-soluble proteinic constituents and cellular-structure-components of a malaria parasite, such as Plasmodium with a detergent solution; and
   b) separating and recovering a polypeptide fraction of said solution having intact polypeptides of molecular weight ranging from about 70,000–85,000 or 90,000–120,000; said polypeptide fraction inducing, in a first splenectomized Saimiri Sciureus monkey, a protective antibody against said strain; said polypeptides being recognized by immunoglobulin from a second Saimiri Sciureus monkey resistant to said strain; said immunoglobulin being capable, by an in vivo passive transfer to a third splenectomized Saimiri Sciureus monkey, sensitive to said strain, of protecting said third monkey against said strain; and c) adding a pharmaceutically acceptable vaccine vehicle.

15. The process of claim 14, wherein the water-soluble proteinic constituents and cellular-structure-components of the starting aqueous solution are derived from a malaria parasite infectious for mouse.

16. The process of claim 14, further comprising contacting the polypeptides either with protective antibodies obtained from said immunized monkeys or with monoclonal antibodies secreted by hybridomas formed from spleen cells of mice immunized with any of said immunogenic polypeptides, to form an antigen-antibody complex, and separating and recovering said antigen from said complex.

17. The process of claim 14, wherein polypeptides of molecular weights ranging from about $72,000 \pm 2,000$ to $90,000 \pm 5000$ are recovered.

* * * * *